US005942432A

United States Patent [19]

Smith et al.

[11] Patent Number: 5,942,432

[45] Date of Patent: Aug. 24, 1999

[54] APPARATUS FOR A FLUID IMPINGEMENT THERMAL CYCLER

[75] Inventors: Douglas H. Smith, Centerville, Del.; John Shigeura, Fremont; Timothy M. Woudenberg, Half Moon Bay, both of Calif.

[73] Assignee: The Perkin-Elmer Corporation, Foster City, Calif.

[21] Appl. No.: 08/946,512

[22] Filed: Oct. 7, 1997

[51] Int. Cl.$^{6}$ .......... C12M 3/00

[52] U.S. Cl. .......... 435/303.1; 435/285.1; 435/287.2; 435/288.4; 236/2; 165/61; 935/77; 935/88

[58] Field of Search .......... 422/129, 131, 422/134, 138; 435/285.1, 287.2, 288.4, 303.1; 263/2; 165/58, 61; 935/77, 88

[56] References Cited

U.S. PATENT DOCUMENTS

| | | | |
|---|---|---|---|
| 5,038,852 | 8/1991 | Johnson et al. | 165/12 |
| 5,187,084 | 2/1993 | Hallsby | 435/91 |
| 5,270,572 | 12/1993 | Nakajima et al. | 257/714 |
| 5,302,347 | 4/1994 | Van Den Berg et al. | 422/67 |
| 5,333,675 | 8/1994 | Mullis et al. | 165/12 |
| 5,455,175 | 10/1995 | Wittwer et al. | 435/286.1 |
| 5,616,301 | 4/1997 | Moser et al. | 422/104 |

FOREIGN PATENT DOCUMENTS

| | | | |
|---|---|---|---|
| WO 95/27198 | 10/1995 | WIPO | G01N 27/447 |

OTHER PUBLICATIONS

A.B. Technology advertisement for The FTS–1s, A New Generation in Rapid Cycling Technology (published prior to the filing of the application) 1.

BioTherm Corporation advertisement for Thermal Cycling in an Air Oven ? Are You Sure? (published prior to the filing of the application) 1.

Florschuetz, L.W. et al., "Heat Transfer Characteristics for Jet Array Impingement with Initial Crossflow," *Journal of Heat Transfer.* 106: 34–41 (1984).

Ganić, E.N. et al., "Basic Concepts of Heat Transfer," from *Handbook of Heat Transfer Fundamentals.* second edition, eds. Rohsenow, W.M. et al., McGraw–Hill Book Company, New York, 1985, 1–9 to 1–12.

Garner, H.R. et al., "High–Throughput PCR," *BioTechniques.* 14: (01) 112–115 (1993).

Guyer, E.C. and Brownell, D.L. (eds.), "Jet Impingement Heat Transfer," from *Handbook of Applied Thermal Design.* McGraw–Hill Book Company, New York, 1989, 1–70 to 1–74.

Hamadah, T.T., "Air Jet Impingement Cooling of an Array of Simulated Electronics Packages," *Heat Transfer in Electronics.* 111: 97–105 (1989).

Hoeskstra, M.F., "Use of a Gas Chromatograph Oven for DNA Amplification by the Polymerase Chain Reaction," *BioTechniques.* 06: (10) 932–936 (1988).

Integrated Separation Systems advertisement for ISS Programmable Oven I (published prior to the filing of the application) 1.

Integrated Separation Systems advertisement for ISS Programmable Oven II (published prior to the filing of the application) 1–2.

(List continued on next page.)

*Primary Examiner*—David A. Redding
*Attorney, Agent, or Firm*—Daniel B. Curtis; Dehlinger & Associates

[57] ABSTRACT

Apparatus are disclosed that thermally cycles samples between at least two temperatures. These apparatus operate by impinging fluid jets onto the outer walls of a sample containing region. Because the impinging fluid jets provide a high heat transfer coefficient between the jet and the sample containing region, the sample containing regions are uniformly cycled between the two temperatures. The heat exchange rate between the jets and the sample regions are substantially uniform.

18 Claims, 4 Drawing Sheets

OTHER PUBLICATIONS

Idaho Technology Inc. advertisement for The 1605 Air Thermo–Cycler Light Speed!(published prior to the filing of the application) 1–4.

Jet Impingement Cooling of Heat Sinks (published prior to the filing of the application) 189–199.

Kays, W.M. and Perkins, H.C., "Forced Convection, Internal Flow in Ducts," *Handbook of Heat Transfer Fundamentals.* second edition, eds. Rohsenow, W.M. et al., McGraw–Hill Book Company, New York, 1985, 7–67 to 7–82.

Kiper, A.M., "Impinging Water Jet Cooling of VLSI Circuits," *Int. Comm. Heat Mass Transfer.* 11: 517–526 (1984).

Oliver, D.G. et al., "Thermal Gradients in Microtitration Plates. Effects on Enzyme–Linked Immunoassay," *Journal of Immunological Methods.* 42: 195–201 (1981).

Perkin Elmer Service Manual for Geneamp PCR System 9600, 7–2 to 7–8, (1991).

Perkin Elmer Cetus advertisement for the Second Generation PCR Technology (published prior to the filing of the application) 1.

Reséndez–Pérez, D. and Barrera–Saldaña, H.A., "Thermocycler Temperature Variation Invalidates PCR Results," *BioTechniques.* 09: (03) 286–294 (1990).

Stratagene advertisement for the RoboCycler™ 40 Temperature Cycler (published prior to the filing of the application) 1.

Wittwer, C.T. et al., "Automated Polymerase Chain Reaction in Capillary Tubes with Hot Air," *Nucleic Acids Research.* 17:(11) 4353–4357 (1989).

Wittwer, C.T. et al., "Minimizing the Time Required for DNA Amplification by Efficient Heat Transfer to Small Samples," *Analytical Biochemistry.* 186: 328–331 (1990).

Wittwer, C.T. and Garling, D.J., "Rapid Cycle DNA Amplification: Time and Temperature Optimization," *BioTechniques.* 10:(01) 76–83 (1991).

Zumbrunnen, D.A. et al., "Convective Heat Transfer Distributions on a Plate Cooled by Planar Water Jets," *Journal of Heat Transfer.* 111: 889–896 (1989).

APPARATUS FOR A FLUID IMPINGEMENT THERMAL CYCLER

BACKGROUND OF THE INVENTION

1. Field of the Invention

This invention relates to a method and apparatus that facilitates the rapid, uniform temperature cycling of samples. More particularly, the invention is directed to an apparatus for performing DNA amplification.

2. Background

There are a variety of investigative settings in which many oligonucleotide or polynucleotide samples, or specific DNA fragments within a sample mixture, are amplified by polymerase chain reaction (PCR). For example, DNA samples contained in the wells of a microtiter plate can be PCR-amplified as an array. In still another setting, it may be desirable to compare the amplification products of one or more DNA fragments contained in different tubes in a tube holder.

If the amplified fragments from the different samples are to be compared, either for fragment size or quantity, it is desirable to conduct the PCR amplification of each sample under substantially identical conditions. This means that the concentration of PCR reagents, as well as the thermal cycling times and temperatures, should be carefully controlled and uniform among all of the samples.

Heretofore, a variety of devices have been used or proposed for carrying out PCR reactions simultaneously in a plurality of structures. Typically, these devices involve a heat block placed against the wells of a microtiter plate, or a heat block designed to hold a plurality of sample tubes. The block, in turn, is alternately heated and cooled by circulating a heating fluid through the block, or by heat conduction to the block. It is difficult to achieve uniform heating and cooling cycles in this type of device, due to uneven heat transfer rate and temperatures within the block and due to the difficulty of providing a good thermal connection between the block and the wells or tubes.

It has also been proposed to circulate a temperature-controlled fluid (such as air or water) past sample tubes as shown by U.S. Pat. No. 5,187,084 to Hallsby. This allows a higher frequency for temperature cycling as the temperature of the flowing fluid is easier to control than that of the block. However, this approach results in temperature gradients on the sample tubes because the fluid flow around a tube causes the temperature of the fluid flowing next to the sample tube to be affected by the temperature of the sample tube itself. Thus, the fluid flow adjacent to the tube at the upstream part of the tube is at a different temperature than the fluid adjacent to the tube at the downstream portion of the tube. In addition, temperature gradients occur within the sample tube because the heat transfer where the fluid impinges the tubes is different from the heat transfer where the fluid flows past the tubes.

SUMMARY OF THE INVENTION

The invention includes an apparatus for thermally cycling a plurality of samples between at least two temperatures. Each of the samples is held in one of a plurality of sample regions in an array. Each of the sample regions in the array defines an outer heat-exchange wall expanse. The apparatus includes a source that provides a pressurized fluid at selected first and second temperatures. The apparatus also includes a chamber that contains a structure adapted to support the array. The chamber contains a manifold that receives the pressurized fluid and distributes the same as a plurality of fluid jets directed against, and substantially normal to, the sample wall expanses, when the array is held by the structure. The pressurized fluid impinging on the wall expanses creates substantially uniform heat exchange between the fluid jets and the samples. The apparatus also includes an outlet for venting the fluid from the fluid jets out of the chamber.

In one aspect, the apparatus includes the array of sample regions, such as a microtiter plate having a plurality of sample wells, or a plurality of tubes held in a tube holder. In an alternative aspect, the apparatus is adapted for use with the array.

The foregoing and many other aspects of the present invention will become more fully apparent when the following detailed description of the preferred embodiments is read in conjunction with the various figures.

DESCRIPTION OF THE PREFERRED EMBODIMENTS

The invention is a high performance thermal cycling device used to uniformly change the temperature of an array of samples. One use for the invention is that of PCR amplification.

Figure 1:
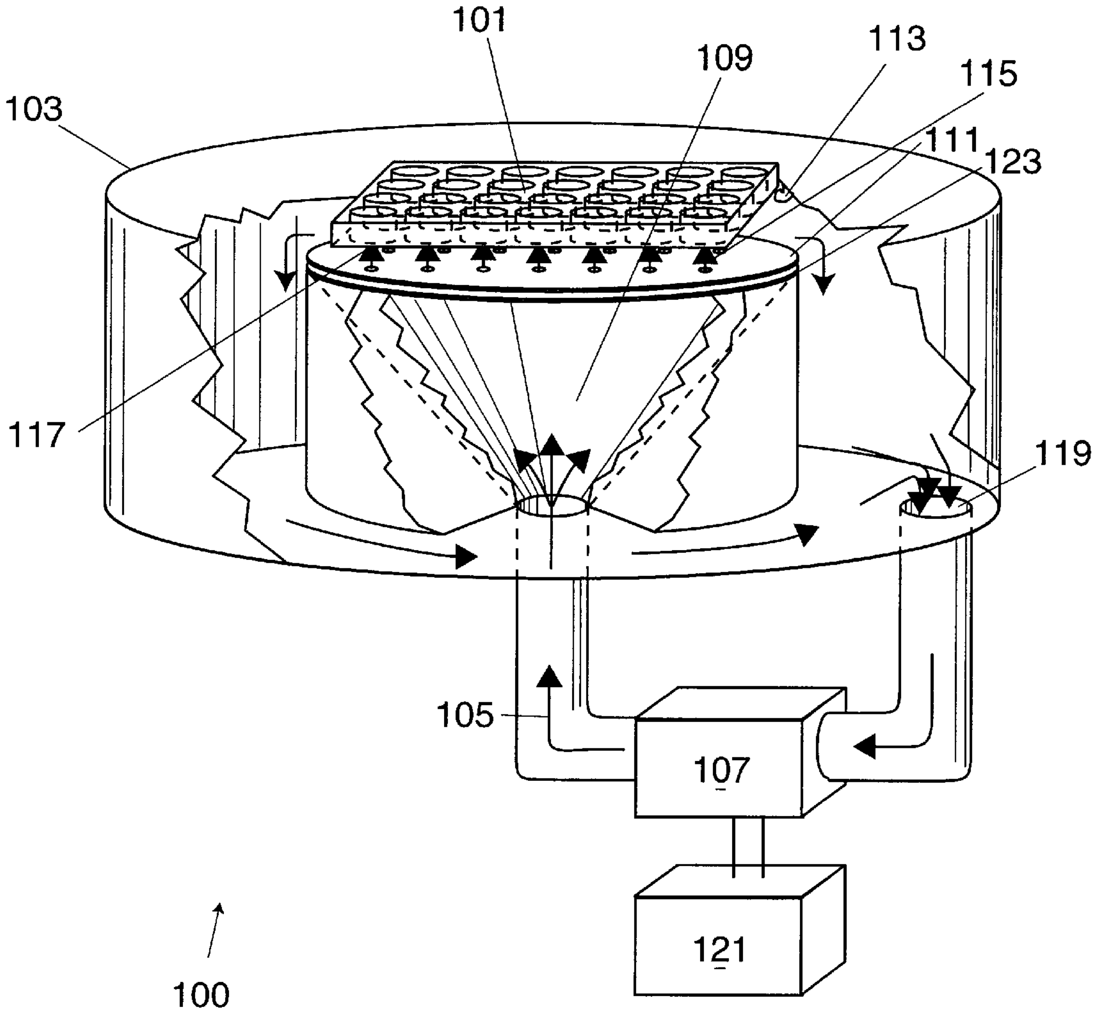
FIG. 1 illustrates an apparatus for thermal cycling an array of samples in accordance with an embodiment of the invention.

FIG. 1 illustrates a thermal cycling apparatus, indicated by general reference character 100, for thermally cycling samples between at least two temperatures. Thermal cycling apparatus 100 is designed to be used with an array 101 that has a plurality of sample regions. Array 101 is subsequently described with respect to FIG. 2. Thermal cycling apparatus 100 includes a closed loop fluid chamber 103 that circulates a pressurized fluid 105. Closed loop fluid chamber 103 is sealed so as to contain the fluid. Pressurized fluid 105 is pressurized by a source 107. Source 107 also adjusts the temperature of pressurized fluid 105. Pressurized fluid 105 enters a manifold 109 that includes an impingement plate 111. In manifold 109 pressurized fluid 105 is uniformly distributed to impingement plate 111. Array 101 is supported in closed loop fluid chamber 103 by a structure 113.

Pressurized fluid 105 flows through holes in impingement plate 111 creating fluid jets 115 (indicated by the arrows extending upward from impingement plate 111) that impinge on an outer heat-exchange wall expanse 117. After fluid jets 115 impinge on outer heat-exchange wall expanse 117 the spent fluid that formed the jets flows to, and through, an outlet 119 to complete the fluid loop to source 107. At source 107, the spent fluid is again pressurized and heated or cooled. Source 107 is controlled by a control unit 121, using methods well understood in the art, and adjusts the temperature and pressure of pressurized fluid 105.

Source 107 contains an impeller (not shown) for pressurizing the spent fluid. It also contains a mechanism (not shown) for heating and cooling the spent fluid. The impeller is positioned after the heating/cooling mechanism so that it thoroughly mixes the temperature controlled spent fluid. Thus, pressurized fluid 105 does not have thermal gradients. To further minimize temperature gradients in pressurized fluid 105 the walls of manifold 109 can be insulated.

In some embodiments, impingement plate 111 can be removed from the rest of manifold 109 and replaced by a differently shaped plate. In other embodiments impingement plate 111 is formed by manifold 109. Further, some embodiments may have a sterile filter 123 within manifold 109 prior to impingement plate 111 to filter pressurized fluid 105.

Figure 2:
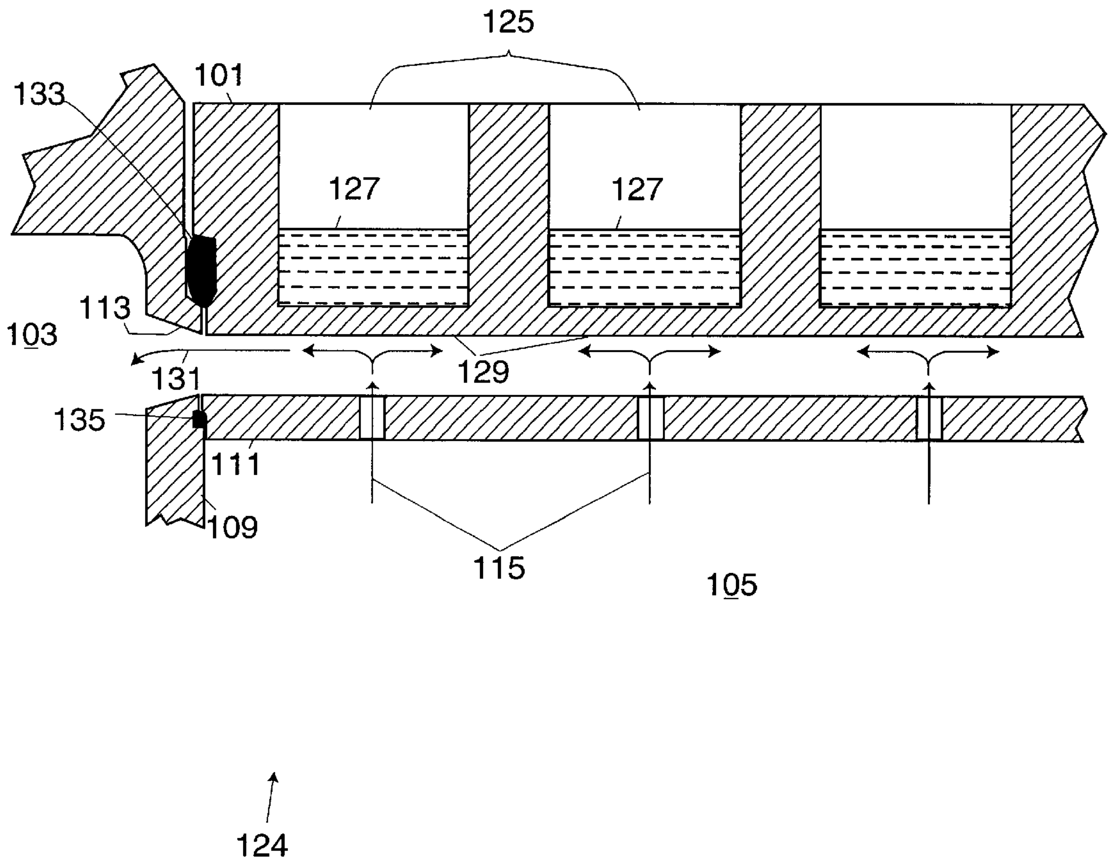
FIG. 2 is an enlarged fragmentary portion of an impingement plate, associated structures and a microtiter plate as used in the FIG. 1 apparatus.

FIG. 2 illustrates an enlarged portion of array 101 of FIG. 1 as indicated by general reference character 124. In this figure, array 101 is a microtiter plate. Microtiter plate 101 has a plurality of wells 125 (the sample regions) for holding a plurality of samples 127 respectively. Each of plurality of wells 125 has a well bottom surface 129. In this embodiment, well bottom surface 129 of each of plurality of wells 125 make up outer heat-exchange wall expanse 117 of thermal cycling apparatus 100 of FIG. 1. Apertures in flat impingement plate 111 generate fluid jets 115. Each of fluid jets 115 impinges on well bottom surface 129 associated with that particular fluid jet. Thus, well bottom surface 129 is tightly coupled (thermally) to the temperature of its respective fluid jet(s).

Spent fluid 131, from fluid jets 115 that has impinged on outer heat-exchange wall expanse 117, flows in a laminar manner past other of plurality of wells 125 to outlet 119. Because the heat transfer between a laminar flow fluid and a surface is several times less than that between a directly impinging fluid and a surface, the temperature of the spent fluid does not affect the temperature of other of plurality of wells 125. The heat transfer from of the impinging fluid jet to the surface also is significantly greater than the heat transfer between the surface and spent fluid 131 even when spent fluid 131 flows past the surface in a fully developed turbulent flow. Thus, each of plurality of wells 125 has the same temperature and there is no significant temperature gradient between any two of plurality of wells 125.

Closed loop fluid chamber 103 is closed by microtiter plate 101 so that the top of microtiter plate 101 is not exposed to the fluid. Microtiter plate 101 is held on closed loop fluid chamber 103 by structure 113 that includes a fluid-tight plate seal 133. Fluid-tight plate seal 133 seals the interface between microtiter plate 101 and closed loop fluid chamber 103 so that the fluid does not escape the chamber. Because microtiter plate 101 is not completely immersed in the fluid, the tops of plurality of wells 125 may be left open or closed with an inexpensive cap. One skilled in the art will understand that if plurality of wells 125 are sealed against the fluid that microtiter plate 101 can be immersed within the fluid.

Each of fluid jets 115 is formed by passing pressurized fluid 105 through an aperture such as an orifice, shaped nozzle, or formed slot in impingement plate 111. Impingement plate 111 is separated from outer heat-exchange wall expanse 117 by a distance that is on the order of two to ten times the width of fluid jets 115 dependent on the fluid use and the desired pressure drop. The pressure of pressurized fluid 105 is such that fluid jets 115 formed by the apertures reach well bottom surface 129 and form fully turbulent flow at well bottom surface 129. The heat transfer efficiency of impinging fluid jets 115 on well bottom surface 129 is a function of the power applied to the impeller. The shape of the apertures that form fluid jets 115 need not be round. One skilled in the art will understand that more than one of the fluid jets 115 may be directed to a particular well bottom surface 129. Conversely, only one of the fluid jets 115 may be directed to impinge on multiple well bottom surfaces so long as the temperature gradients between the well bottom remain within tolerance.

In addition, one skilled in the art will understand that impingement plate 111 can be constructed to be removed from manifold 109 or formed as part of manifold 109. In the embodiment shown in FIG. 2 impingement plate 111 is removable from manifold 109 and the resulting interface is sealed by a fluid-tight manifold seal 135.

Figure 3:
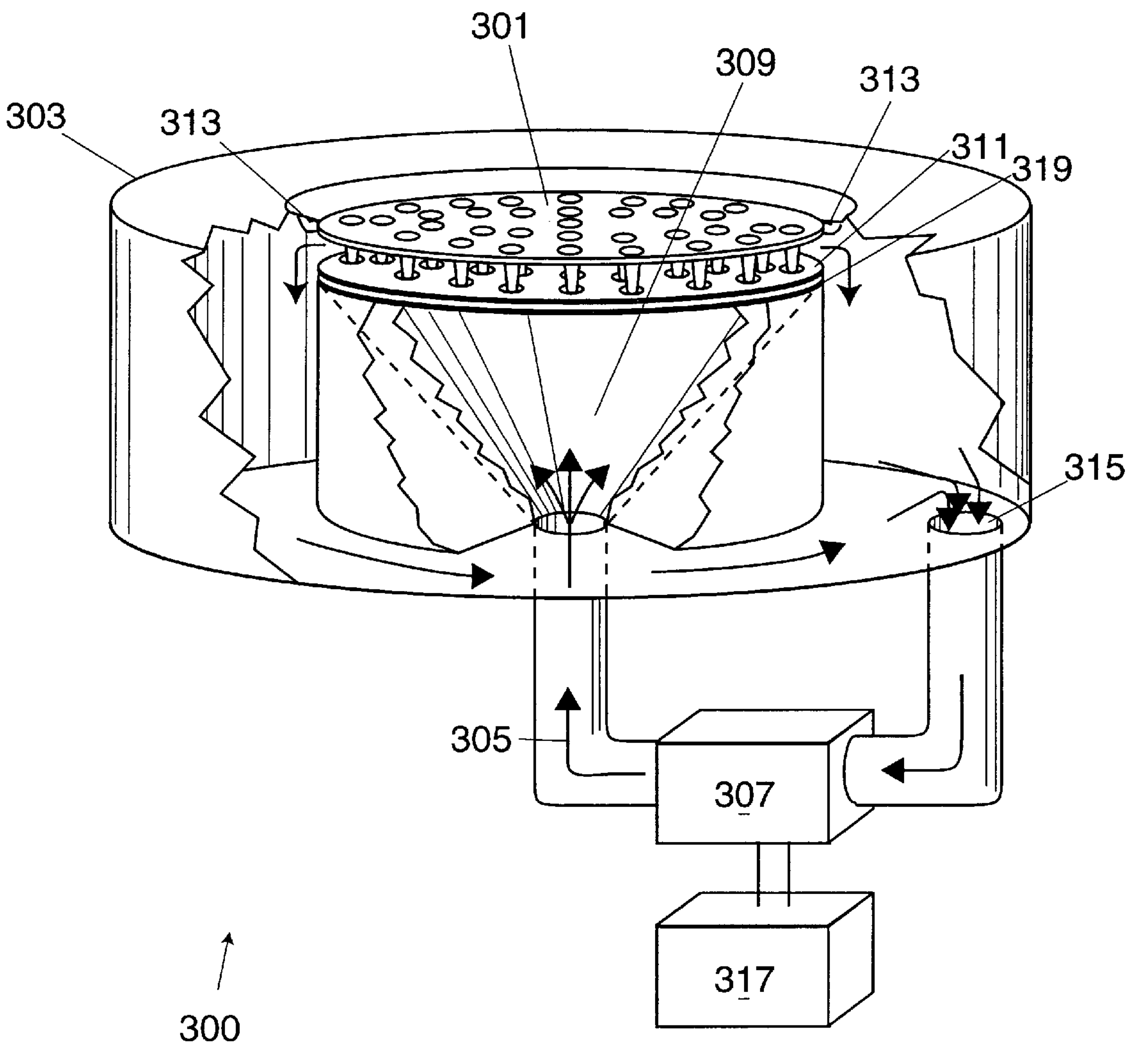
FIG. 3 illustrates an apparatus for thermal cycling an array of samples within tubes in accordance with an embodiment of the invention.

FIG. 3 illustrates a thermal cycling apparatus, indicated by general reference character 300, for thermally cycling samples held in tubes between at least two temperatures. Thermal cycling apparatus 300 is designed to be used with a tube array 301 that uses a plurality of tubes as the sample regions. Tube array 301 is subsequently described with respect to FIG. 4. Thermal cycling apparatus 300 includes a closed loop fluid chamber 303 that circulates a pressurized fluid 305. Closed loop fluid chamber 303 is sealed so as to contain the fluid. Pressurized fluid 305 is pressurized by a source 307. Source 307 also adjusts the temperature of pressurized fluid 305. Pressurized fluid 305 enters a manifold 309 that incorporates a shaped impingement plate 311. Tube array 301 is supported in closed loop fluid chamber 303 by a structure 313 such that each of the tubes in tube array 301 extend into a pocket (shown in, and subsequently described with respect to FIG. 4) formed by shaped impingement plate 311. Pressurized fluid 305 is uniformly distributed to shaped impingement plate 311 by manifold 309. Pressurized fluid 305 flows through holes in shaped impingement plate 311 creating fluid jets (shown in, and subsequently described with respect to FIG. 4). The spent fluid that formed the fluid jets flows to, and through, an outlet 315 to complete the fluid loop to source 307. At source 307, the spent fluid is again pressurized and heated or cooled. Source 307 is controlled by a control unit 317, using methods well understood in the art, and adjusts the temperature and pressure of pressurized fluid 305.

Some embodiments may have a sterile filter 319 within manifold 309 prior to shaped impingement plate 311 to filter pressurized fluid 305.

Source 307 contains an impeller (not shown) for pressurizing the spent fluid. It also contains a mechanism (not shown) for heating and cooling the spent fluid. The impeller thoroughly mixes the spent fluid so that pressurized fluid 305 does not have thermal gradients. The impeller is positioned after the heating/cooling mechanism so that it thoroughly mixes the temperature controlled spent fluid. Thus, pressurized fluid 305 does not have thermal gradients. To further minimize temperature gradients in pressurized fluid 305 the walls of manifold 309 can be insulated.

Figure 4:
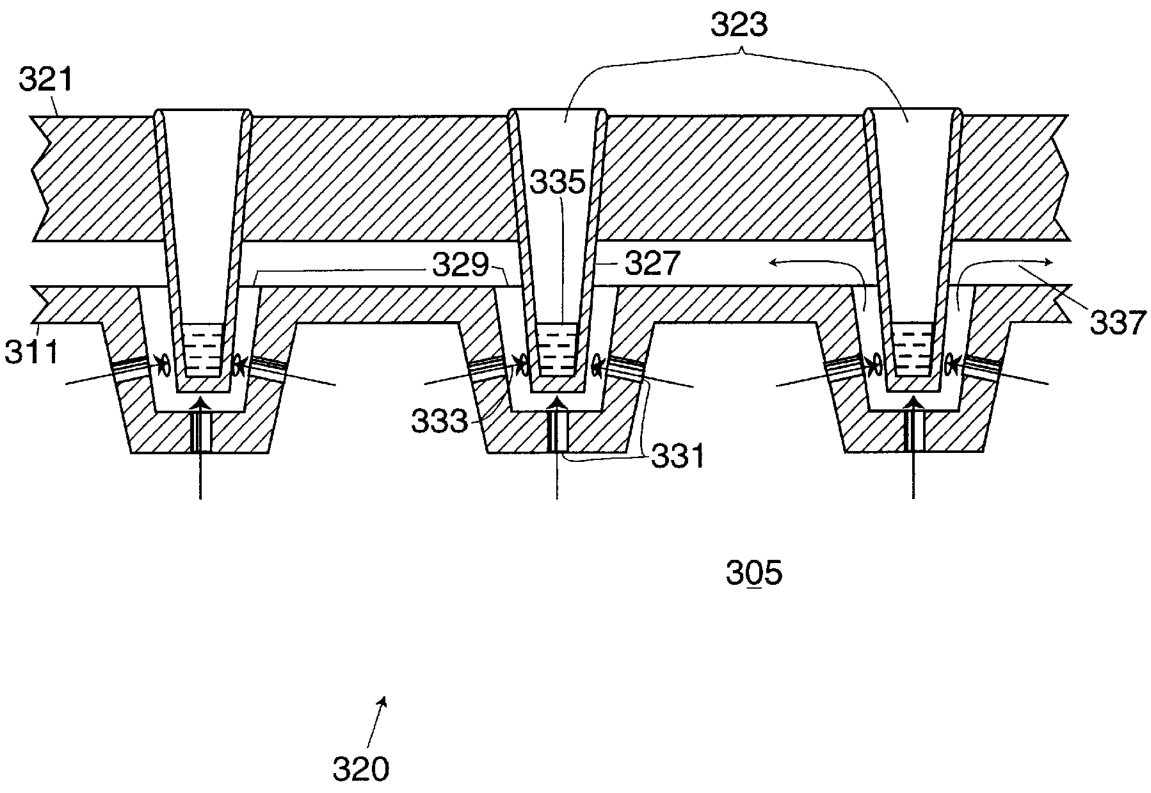
FIG. 4 is an enlarged fragmentary portion of an shaped impingement plate, associated structures and tube array as used in the FIG. 3 apparatus.

FIG. 4 illustrates an enlarged portion of tube array 301 of FIG. 3 as indicated by general reference character 320, that includes a support plate 321 that rigidly holds a plurality of tubes 323 in tube array 301. In the embodiment shown, each of plurality of tubes 323 is molded in support plate 321. One skilled in the art will understand that other techniques exist to rigidly attach each of plurality of tubes 323 to support plate 321 such as by the use of a threaded connection.

Each of plurality of tubes 323 has an elongated sample-holding portion 327 that extends into one of a plurality of pockets 329 formed by shaped impingement plate 311. Each of plurality of pockets 329 has one or more apertures 331 each of which form a fluid jet 333, from pressurized fluid 305) that impinges on elongated sample-holding portion 327 of one of plurality of tubes 323 at approximately ninety degrees from the surface of elongated sample-holding portion 327. The outside of elongated sample-holding portion 327 is the outer heat exchange wall expanse. Impinging fluid jet 333 on the outer heat-exchange wall expanse efficiently transfers heat between fluid jet 333 and the outer heat-exchange wall expanse. Each of plurality of tubes 323 holds a sample 335 that is cycled between at least two temperatures dependent on the temperature of fluid jet 333. Spent fluid 337 from fluid jet 333 flows out of each of plurality of pockets 329 and past the non-sample-holding portion of plurality of tubes 323 in a laminar-flow manner. Because the heat transfer coefficients of a laminar flow is so much less than that of an impinging flow, the spent fluid does not affect the temperature of the samples held in the other tubes. The heat transfer from of the impinging fluid jet to the surface also is significantly greater than the heat transfer between the surface and spent and spent fluid 337 even when spent fluid 337 flows past the surface in a fully developed turbulent flow. The fluid jets have a jet dimension. The diameter of the fluid jets range from 0.5 mm to approximately 2 mm depending on the fluid used and the pressure drop desired. Elongated sample-holding portion 327 is separated from the walls of one of plurality of pockets 329 by a distance on the order of two to ten times the jet diameter.

It will be appreciated from the foregoing that tube array 301 can be fully immersed within the fluid if plurality of tubes 323 are securely closed. In addition, one skilled in the art will understand that shaped impingement plate 311 can be constructed to be removed from manifold 309 or formed as part of manifold 309. In the embodiment shown in FIG. 3, shaped impingement plate 311 is formed as part of manifold 309. One skilled in the art will understand that some embodiments allow the different impingement plates to be interchangeable on the manifold. This allows the apparatus to be adapted to array configurations other than the ones describe herein.

It will be appreciated from the forgoing that the apparatus can be provided without the sample array and that the apparatus can be used with existing tubes, microtiter plates, or other similar sample-holding mechanisms. Because the heat transfer is a result of fluid jets impinging a surface, one skilled in the art will also understand that there is no need to attempt to form a high quality thermal seal between a thermal block and a sample container. Thus, the wall expanse can be irregular and does not rely on a mechanical contact thermal conduction path. It will also be appreciated that the invention contemplates many impingement jet configuration other than those described above. In particular, but without limitation, the invention contemplates applying impinging jets on both sides of a microtiter plate, to the lid of closed sample containers and to wells micro-machined in silicon or stamped in plastic.

The fluids most commonly used within the invention will be a gas, such as air, and a high heat capacity liquid, such as water. Liquid is the preferred fluid when using smaller geometry arrays or with rapid temperature ramp rates. In addition, a non-compressible liquid may be preferred if the temperature of the fluid jet is critical as a compressible gas cool as it expands and the temperature control mechanism does not take this cooling into account.

From the foregoing, it will be appreciated that the invention has the following advantages:

1. Direct heat exchange between the fluid and each sample region so as to eliminate temperature gradients between the sample regions.

2. A fluid jet impinging at substantially ninety degrees to the heat exchange surface provides a more rapid and efficient heat transfer between the surface and the fluid than does laminar fluid flow adjacent to the heat exchange surface. Because the spent fluid from the impinging jets flows past other sample regions in such a laminar flow, the other sample regions are not affected by the temperature of the spent fluid. Thus, reducing temperature gradients between the sample regions in the array.

3. Allows precise controlled, uniform thermal cycling among separate sample regions such as a plurality of wells or tubes. This allows PCR amplification of separate samples under substantially identical conditions.

Although the present invention has been described in terms of the presently preferred embodiments, one skilled in the art will understand that various modifications and alterations may be made without departing from the scope of the invention. Accordingly, the scope of the invention is not to be limited to the particular invention embodiments discussed herein, but should be defined only by the appended claims and equivalents thereof.

What is claimed is:

1. An apparatus for thermally cycling a plurality of samples between at least two temperatures where each of said samples is held in one of a plurality of sample regions in an array, where each of said sample regions defines an outer heat-exchange wall expanse, said apparatus comprising:

a source for providing a pressurized fluid at a selected first and second temperatures; and a chamber containing:

(a) a structure adapted for supporting said array;

(b) a manifold for receiving said pressurized fluid and distributing same in the form of a plurality of fluid jets directed against said wall expanses, and substantially normal thereto, when said array is held by said structure, to produce substantially uniform heat exchange between said fluid jets and said samples; and (c) an outlet for venting said fluid from said fluid jets out of said chamber.

2. The apparatus of claim 1 for use with a microtiter plate, comprising said array, wherein said sample regions are composed of a plurality of wells each having a bottom surface defining said wall expanse wherein said fluid jets impinge on said bottom surface when said plate is held by said structure.

3. The apparatus of claim 1 for use with a plurality of tubes, comprising said array, each of said tubes having an elongated sample-holding portion defining said wall expanse and said manifold having a plurality of pockets each adapted to enclose said wall expanse of one of said tubes;

each of said pockets distributing said fluid jets onto said wall expanse, said pockets open at the top to allow said fluid from said fluid jets to exit said pockets; and said structure comprising a plate adapted to support said tubes descending into said pockets.

4. The apparatus of claim 1, wherein said samples are polynucleotides and said apparatus is used for thermal cycling a polymerase chain reaction.

5. The apparatus of claim 1 further comprising fluid recycling means operativily connecting said outlet to said source for recycling said fluid there between.

6. The apparatus of claim 5 further comprising a sterile filter to filter said fluid.

7. The apparatus of claim 1, wherein said structure is adapted to form a fluid-tight seal between the structure and the array.

8. The apparatus of claim 1, wherein said pressurized fluid is a liquid.

9. The apparatus of claim 1, wherein said pressurized fluid is a gas.

10. An apparatus for thermally cycling a plurality of samples between at least two temperatures comprising:

a source for providing a pressurized fluid at a selected first and second temperatures; and a chamber containing:

(a) an array of a plurality of sample regions where each of said samples is adapted to be held in one of said sample regions and each of said sample regions defines an outer heat-exchange wall expanse;

(b) a structure supporting said array;

(c) a manifold for receiving said pressurized fluid and distributing same in the form of a plurality of fluid jets directed against said wall expanses and substantially normal thereto, to produce substantially uniform heat exchange between said fluid jets and said samples; and (d) an outlet for venting said fluid from said fluid jets out of said chamber.

11. The apparatus of claim 10 wherein said array is contained in a microtiter plate wherein said sample regions are composed of a plurality of wells, each having a bottom surface defining said wall expanse wherein said fluid jets impinge on said bottom surface.

12. The apparatus of claim 10 wherein said array is formed by a plurality of tubes, each of said tubes having an elongated sample-holding portion defining said wall expanse and said manifold having a plurality of pockets each adapted to enclose said wall expanse of one of said tubes;

each of said pockets distributing said fluid jets onto said wall expanse, said pockets open at the top to allow said fluid from said fluid jets to exit said pockets; and said structure comprising a plate to support said tubes descending into said pockets.

13. The apparatus of claim 10 wherein said samples are polynucleotides and said apparatus is used for thermal cycling a polymerase chain reaction.

14. The apparatus of claim 10 further comprising fluid recycling means operativily connecting said outlet to said source for recycling said fluid there between.

15. The apparatus of claim 14 further comprising a sterile filter to filter said fluid.

16. The apparatus of claim 10, wherein said structure is adapted to form a fluid-tight seal between the structure and the array.

17. The apparatus of claim 10, wherein said pressurized fluid is a liquid.

18. The apparatus of claim 10, wherein said pressurized fluid is a gas.

* * * * *